United States Patent
Hutchinson et al.

(10) Patent No.: US 10,806,354 B2
(45) Date of Patent: Oct. 20, 2020

(54) METHOD AND APPARATUS FOR ESTIMATING HEART RATE

(71) Applicant: Oxehealth Limited, Oxford (GB)

(72) Inventors: Nicholas Dunkley Hutchinson, Oxford (GB); Simon Mark Chave Jones, Oxford (GB); Muhammad Fraz, Oxford (GB)

(73) Assignee: OXEHEALTH LIMITED, London (GB)

( * ) Notice: Subject to any disclaimer, the term of this patent is extended or adjusted under 35 U.S.C. 154(b) by 104 days.

(21) Appl. No.: 16/071,611

(22) PCT Filed: Jan. 23, 2017

(86) PCT No.: PCT/GB2017/050162
§ 371 (c)(1),
(2) Date: Jul. 20, 2018

(87) PCT Pub. No.: WO2017/125763
PCT Pub. Date: Jul. 27, 2017

(65) Prior Publication Data
US 2019/0029543 A1    Jan. 31, 2019

(30) Foreign Application Priority Data

Jan. 21, 2016  (GB) .................................. 1601140.5

(51) Int. Cl.
*G06K 9/00*  (2006.01)
*A61B 5/024*  (2006.01)
(Continued)

(52) U.S. Cl.
CPC ........ *A61B 5/02405* (2013.01); *A61B 5/0077* (2013.01); *A61B 5/02416* (2013.01);
(Continued)

(58) Field of Classification Search
CPC combination set(s) only.
See application file for complete search history.

(56) References Cited

U.S. PATENT DOCUMENTS 8,855,384 B2   10/2014   Kyal et al.
8,965,090 B1    2/2015   Khachaturian et al.
(Continued)

FOREIGN PATENT DOCUMENTS

EP   0615245 A2   9/1994
EP   0919184 A1   6/1999
(Continued)

OTHER PUBLICATIONS

Pisani, Francesco et al. "Real-time automated detection of clonic seizures in newborns." Clinical Neurophysiology, (2014) http://dx.doi.org/10.1016/j.clinph.2013.12.119.
(Continued)

*Primary Examiner* — Alex Kok S Liew
(74) *Attorney, Agent, or Firm* — Harness, Dickey & Pierce, P.L.C.

(57) ABSTRACT

A method and apparatus for estimating heart rate of a subject from a video image of the subject. Regions of interest are generated by: detecting and tracking feature points through the video image sequence, triangulating the feature points and generating square regions of interest corresponding to the in-circles of the triangles; or, according to size and location probability distributions which are defined to have a high probability for image areas away from strong intensity gradients and which generate good quality signals. In an alternative embodiment, the intensity variations from the square regions of interest through the frame sequence are taken as time series signals and those signals which have a strong peak in the power spectrum are selected and subject to principal component analysis. The principal component
(Continued)

with a highest signal quality is selected and its frequency is found and used to estimate the heart rate.

19 Claims, 10 Drawing Sheets

(51) Int. Cl.
    *A61B 5/00*         (2006.01)
    *G06T 7/00*         (2017.01)
    *G06T 7/246*       (2017.01)
    *G06T 7/269*       (2017.01)

(52) U.S. Cl.
    CPC .......... *A61B 5/7485* (2013.01); *G06T 7/0016* (2013.01); *G06T 7/246* (2017.01); *G06T 7/269* (2017.01); *A61B 2576/023* (2013.01); *G06K 9/00261* (2013.01); *G06T 2207/10016* (2013.01); *G06T 2207/30076* (2013.01)

(56) References Cited

U.S. PATENT DOCUMENTS

| | | |
|---|---|---|
| 9,036,877 B2 | 5/2015 | Kyal et al. |
| 10,034,979 B2 | 7/2018 | Bechtel et al. |
| 10,292,662 B2 | 5/2019 | Kirenko |
| 2002/0106709 A1 | 8/2002 | Potts et al. |
| 2002/0180870 A1 | 12/2002 | Chen |
| 2003/0138149 A1 | 7/2003 | Iizuka et al. |
| 2003/0228032 A1* | 12/2003 | Rui .................. G06K 9/00234 382/103 |
| 2005/0197590 A1 | 9/2005 | Osorio et al. |
| 2006/0058618 A1 | 3/2006 | Nishiura |
| 2007/0156060 A1 | 7/2007 | Cervantes |
| 2007/0195931 A1 | 8/2007 | Ohishi |
| 2008/0292151 A1 | 11/2008 | Kurtz et al. |
| 2009/0216499 A1 | 8/2009 | Tobola et al. |
| 2010/0049064 A1 | 2/2010 | Bodmer et al. |
| 2010/0074475 A1* | 3/2010 | Chouno ................. A61B 5/055 382/107 |
| 2010/0298656 A1 | 11/2010 | McCombie et al. |
| 2011/0046498 A1 | 2/2011 | Klap et al. |
| 2011/0150274 A1* | 6/2011 | Patwardhan .......... G06T 7/0012 382/103 |
| 2011/0251493 A1 | 10/2011 | Poh et al. |
| 2011/0311143 A1 | 12/2011 | Cennini et al. |
| 2012/0141000 A1 | 6/2012 | Jeanne et al. |
| 2012/0213405 A1* | 8/2012 | Sasaki ................ G06K 9/00791 382/103 |
| 2012/0242819 A1 | 9/2012 | Schamp |
| 2013/0138009 A1 | 5/2013 | Nierenberg et al. |
| 2013/0324875 A1 | 12/2013 | Mestha et al. |
| 2014/0003690 A1 | 1/2014 | Razeto et al. |
| 2014/0023235 A1 | 1/2014 | Cennini et al. |
| 2014/0037163 A1 | 2/2014 | Kirenko et al. |
| 2014/0037166 A1 | 2/2014 | De Haan et al. |
| 2014/0236036 A1 | 8/2014 | de Haan et al. |
| 2014/0276099 A1 | 9/2014 | Kirenko et al. |
| 2014/0276104 A1 | 9/2014 | Tao et al. |
| 2014/0334697 A1 | 11/2014 | Kersten et al. |
| 2014/0371599 A1 | 12/2014 | Wu et al. |
| 2014/0371635 A1 | 12/2014 | Shinar et al. |
| 2014/0378842 A1 | 12/2014 | Xu et al. |
| 2015/0005646 A1 | 1/2015 | Balakrishnan et al. |
| 2015/0063708 A1 | 3/2015 | Sripadarao et al. |
| 2015/0148687 A1 | 5/2015 | Kitajima et al. |
| 2015/0208987 A1 | 7/2015 | Shan et al. |
| 2015/0221069 A1 | 8/2015 | Shaburova et al. |
| 2015/0250391 A1 | 9/2015 | Kyal et al. |
| 2015/0363361 A1 | 12/2015 | Kniazev |
| 2016/0106340 A1 | 4/2016 | Mestha et al. |
| 2016/0125260 A1 | 5/2016 | Huang et al. |
| 2016/0132732 A1 | 5/2016 | Gunther et al. |
| 2016/0220128 A1 | 8/2016 | Den Brinker et al. |
| 2016/0253820 A1 | 9/2016 | Jeanne et al. |
| 2016/0310067 A1 | 10/2016 | Heinrich et al. |
| 2017/0007185 A1 | 1/2017 | Lin et al. |
| 2017/0042432 A1 | 2/2017 | Adib et al. |
| 2017/0224256 A1 | 8/2017 | Kirenko |
| 2017/0238805 A1 | 8/2017 | Addison et al. |
| 2017/0238842 A1 | 8/2017 | Jacquel et al. |
| 2018/0085010 A1 | 3/2018 | Jones et al. |
| 2018/0279885 A1 | 10/2018 | Bulut |
| 2019/0000391 A1 | 1/2019 | De Haan et al. |
| 2019/0267040 A1 | 8/2019 | Ikeda et al. |

FOREIGN PATENT DOCUMENTS

| | | |
|---|---|---|
| EP | 1571594 A2 | 9/2005 |
| EP | 2767233 A1 | 8/2014 |
| EP | 2976998 A1 | 1/2016 |
| EP | 2988274 A2 | 2/2016 |
| EP | 3073905 A1 | 10/2016 |
| EP | 3207862 A1 | 8/2017 |
| JP | 2011130996 A | 7/2011 |
| WO | WO-2010/100593 A1 | 9/2010 |
| WO | WO-2010/115939 A2 | 10/2010 |
| WO | WO-2011021128 A2 | 2/2011 |
| WO | WO-2013/027027 A2 | 2/2013 |
| WO | WO-2014/125250 A1 | 8/2014 |
| WO | WO-2014131850 A1 | 9/2014 |
| WO | WO-2014140994 A1 | 9/2014 |
| WO | WO-201504915 A1 | 1/2015 |
| WO | WO-2015/049150 A1 | 4/2015 |
| WO | WO-2015055709 A1 | 4/2015 |
| WO | WO-2015/078735 A1 | 6/2015 |
| WO | WO-2015/091582 A1 | 6/2015 |
| WO | WO-2015172735 A1 | 11/2015 |
| WO | WO-2016092290 A1 | 6/2016 |
| WO | WO-2016094749 A1 | 6/2016 |
| WO | WO-2016159151 A1 | 10/2016 |
| WO | WO-2017125743 A1 | 7/2017 |
| WO | WO-2017125744 A1 | 7/2017 |
| WO | WO-2017125763 A1 | 7/2017 |

OTHER PUBLICATIONS

International Search Report for PCT/GB2017/050162, ISA/EP, Rijswijk, NL, dated Jul. 6, 2017.
Written Opinion of the ISA for PCT/GB2017/050162, ISA/EP, Rijswijk, NL, dated Jul. 6, 2017.
Search Report for Priority Application GB1601140.5, UK IPO, Newport, South Wales, dated Jul. 21, 2016.
Verkruysse et al., "Remote Plethysmographic imaging using ambient light", Optics Express, 16(26), Dec. 22, 2008, pp. 21434-21445.
Mayank Kumar et al, DistancePPG: Robust non-contact vital signs monitoring using a camera, Biomedical Optics Express, 2015, pp. 1565-1588.
Nathalie M. El Nabbout et al, "Automatically Detecting and Tracking People Walking through a Transparent Door with Vision", Computer and Robot Vision, 2008. CRV '08. Canadian Conference on, IEEE, Piscataway, NJ, USA, May 28, 2008 (May 28, 2008), pp. 171-178.
Qiang Zhu et al, "Learning a Sparse, Corner-Based Representation for Corner-Based Representation for Time-varying Background Modeling" , Computer Vision, 2005. ICCV 2005. Tenth IEEE International Conference on Beijing, China Oct. 17-20, 2005, Piscataway, NJ, USA, IEEE, Los Alamitos, CA, USA, vol. 1, Oct. 17, 2005 (Oct. 17, 2005), pp. 678-685.
Konstantinos Avgerinakis et al, "Activity detection and recognition of daily living events", Proceedings of the 1st ACM International Workshop on Multimedia Indexing and Information Retrieval for Healthcare, MIIRH '13, Oct. 22, 2013 (Oct. 22, 2013), pp. 1-7.
Arindam Sikdar et al, "Computer-Vision-Guided Human Pulse Rate Estimation: A Review", IEEE Reviews in Biomedical Engineering, vol. 9, Sep. 16, 2016 (Sep. 16, 2016), pp. 91-105.
Yu Sun et al,"Photoplethysmography Revisited: From Contact to Noncontact, From Point to Imaging", IEEE Transactions on Biomedical Engineering, IEEE Service Center, Piscataway, NJ, USA, vol. 63, No. 3, Mar. 1, 2016 (Mar. 1, 2016), pp. 463-477.

(56) References Cited

OTHER PUBLICATIONS

Tongchi Zhou et al, "A study of relative motion point trajectories for action recognition", 2015 International Conference on Wireless Communications & Signal Processing (WCSP), IEEE, Oct. 15, 2015 (Oct. 15, 2015), pp. 1-5.
Hisato Aota et al, "Extracting objects by clustering of full pixel trajectories", Signal Processing and Multimedia Applications (SIGMAP), Proceedings of the 2010 International Conference on, IEEE, Jul. 26, 2010 (Jul. 26, 2010), pp. 65-72.
Shandong Wu et al, "A hierarchical motion trajectory signature descriptor", 2008 IEEE International Conference on Robotics and Automation. The Half-Day Workshop on: Towards Autonomous Agriculture of Tomorrow, IEEE—Piscataway, NJ, USA, Piscataway, NJ, USA, May 19, 2008 (May 19, 2008), pp. 3070-3075.
Search Report for GB Application No. 1618828.6, dated Mar. 31, 2017.
International Search Report and Written Opinion for PCT/GB2017/053343, dated Jan. 4, 2018; ISA/EP.
International Search Report and Written Opinion for PCT/GB2017/052779, dated Nov. 10, 2017; ISA/EP.
Search Report for GB Application No. 1615899.0, dated Feb. 28, 2017.
International Preliminary Report on Patentability and Written Opinion regarding Applicaiton No. PCT/GB2017/052779 dated Mar. 19, 2019.
International Search Report for PCT/GB2017/050127, ISA/EP, Rijswijk, NL, dated Mar. 28, 2017.
Written Opinion of the ISA for PCT/GB2017/050127, ISA/EP, Rijswijk, NL, dated Mar. 28, 2017.
UK IPO Search Report under Section 17(5) for priority application GB1061143.9, dated Mar. 30, 2016.
International Search Report for PCT/GB2017/050128, ISA/EP, Rijswijk, NL, dated Apr. 13, 2017.
Written Opinion of the ISA for PCT/GB2017/050128, ISA/EP, Rijswijk, NL, dated Apr. 13, 2017.
Search Report under Section 17(5) for priority application GB1601142.1, UKIPO, Newport, South Wales, dated Jun. 28, 2016.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
International Search Report for PCT/GB2017/050126, ISA/EP, Rijswijk, NL, dated Apr. 20, 2017.
Written Opinion of the ISA for PCT/GB2017/050126, ISA/EP, Rijswijk, NL, dated Apr. 20, 2017.
UK IPO Search Report for GB priority application 1601217.1, Newport, South Wales, dated Jul. 25, 2016.
Search Report regarding United Kingdom Patent Application No. GB1706449.4, dated Oct. 25, 2017.
Amelard Robert et al. "Illumination-compensated non-contact imaging photoplethysmography via dual-mode temporally coded illumination". Progress in Biomedical Optics and Imaging, SPIE—International Society for Optical Engineering, Bellingham, WA, US., vol. 9316, Mar. 5, 2015.
Blocker Timon et al, "An online PPGI approach for camera based heart rate monitoring using beat-to-beat detection", 2017 IEEE Sensors Applications Symposium (SAS), IEEE, Mar. 13, 2017.
Extended European Search Report regarding applicaiton No. 18168310.3-1115 dated Oct. 1, 2018.
European Search Report regarding Application No. EP 19 15 8085 dated Jul. 10, 2019.
Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).
Search Report of UKIPO regarding Application No. GB1900033.0 dated Jun. 13, 2019.
British Search Report regarding Appliction No. 1900034.8 dated Jun. 13, 2019.
Extended EP Search Report regarding Application No. 19220090.5 dated Feb. 24, 2020.
U.S. Appl. No. 16/732,769, filed Jan. 2, 2020, Nicholas Dunkley Hutchinson.
U.S. Appl. No. 16/732,979, filed Jan. 2, 2020, Nicholas Dunkley Hutchinson.
U.S. Appl. No. 16/733,065, filed Jan. 2, 2020, Nicholas Dunkley Hutchinson.
U.S. Appl. No. 15/961,279, filed Apr. 24, 2018, Nicholas Dunkley Hutchinson.
U.S. Appl. No. 16/071,542, filed Jul. 20, 2018, Nicholas Dunkley Hutchinson.
U.S. Appl. No. 16/071,570, filed Jul. 20, 2018, Simon Mark Chave Jones.
U.S. Appl. No. 16/071,591, filed Jul. 20, 2018, Muhammad Fraz.
U.S. Appl. No. 16/291,728, filed Mar. 4, 2019, Nicholas Dunkley Hutchinson.
U.S. Appl. No. 16/334,211, filed Mar. 18, 2019, Mohamed Elmikaty.
U.S. Appl. No. 16/347,925, filed May 7, 2019, Simon Mark Chave Jones.

\* cited by examiner

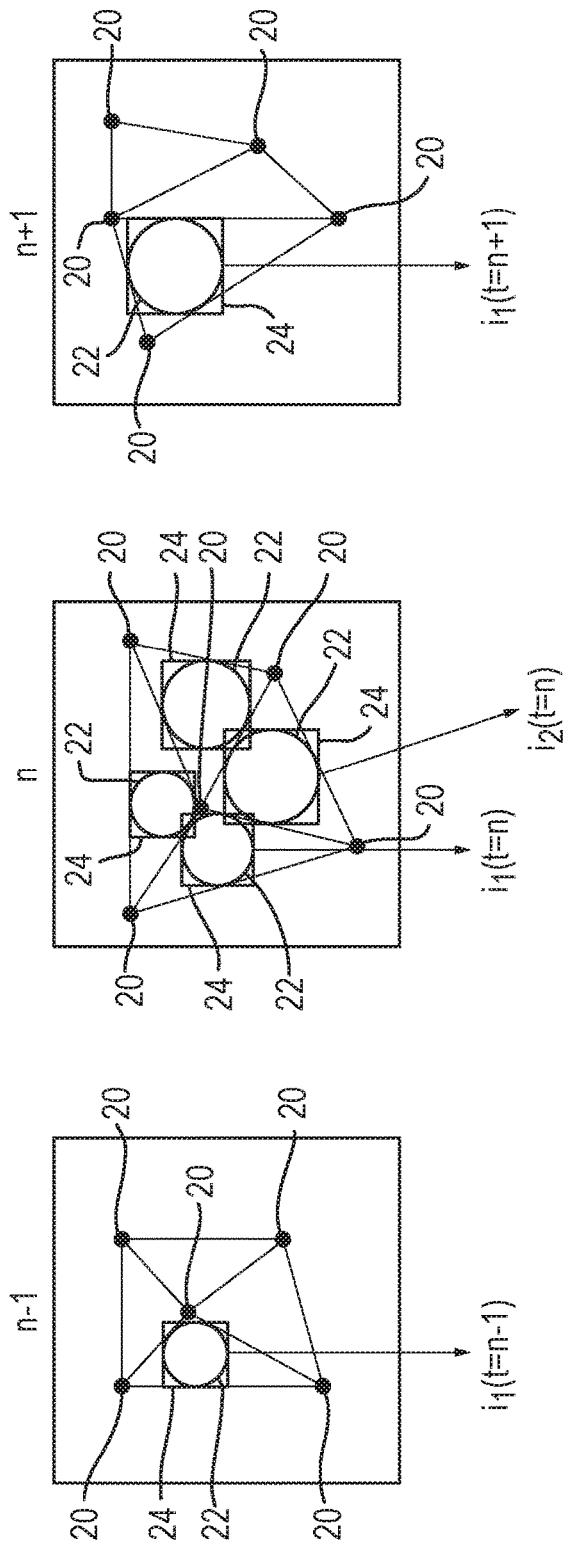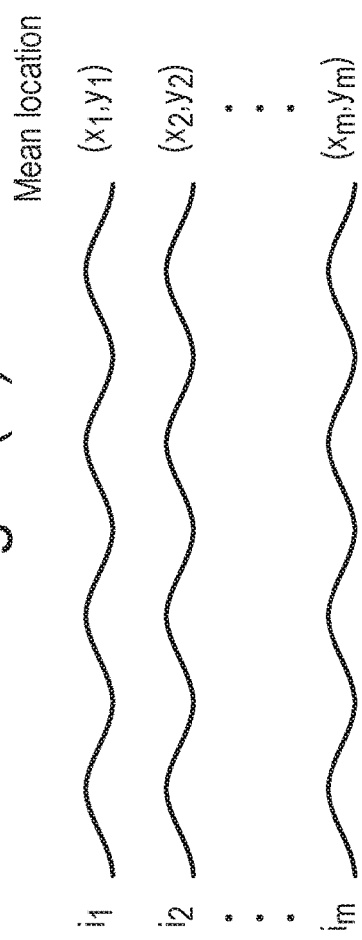

Starting point is square locations and intensities

METHOD AND APPARATUS FOR ESTIMATING HEART RATE

CROSS-REFERENCE TO RELATED APPLICATIONS

This application is a 371 U.S. National Stage of International Application No. PCT/GB2017/050162, filed Jan. 23, 2017, which claims priority to British Patent Application No. 1601140.5, filed Jan. 21, 2016. The entire disclosures of the above applications are incorporated herein by reference.

The present invention relates to a method and apparatus for estimating the heart rate of a subject, in particular for analysing video signals from a video camera taking a video image which includes the subject and detecting a photoplethysmographic signal therein.

Over recent years techniques have been developed for obtaining an estimate of the heart rate of a human or animal subject which are less intrusive than those using traditional contact sensors, such as electrocardiogram (ECG) sensors or photoplethysmogram (PPG) finger or ear probes. For example Verkruysse et al., "Remote plethysmographic imaging using ambient light", Optics Express, 16 (26), 22 Dec. 2008, PP. 21434-21445 demonstrated that photoplethysmographic signals could be detected in the video signal from a conventional consumer standard video camera where a human subject was illuminated under ambient light.

This idea has been developed further in, for example, WO-A2-2013/027027 and WO-A1-2015/049150 which aim to increase the reliability of the detection of the remote PPG signal. The paper "Distance PPG: robust non-contact vital signs monitoring using a camera" by Mayank Kumar et al.; 6 Apr. 2015; Biomedical Optics Express 1565, 1 May 2015, Vol. 6 No. 5, discusses a method of combining skin-colour change signals from different tracked regions of a subject's face using a weighted average, where the weights depend on the blood perfusion and incident light density in the region to improve the signal-to-noise ratio of the camera-based estimate. It discusses the various challenges for camera-based non-contact vital sign monitoring and proposes that improvements in the signal-to-noise ratio of the camera-based estimates reduces the errors in vital sign estimation.

Many of the prior art techniques have been based on careful control of the subject being monitored and the lighting conditions in the environment. Thus, although they claim success in detecting the heart rate or vital signs of the subject, in general the subjects were required to remain relatively still, the subjects were not obscured and the lighting conditions were kept relatively constant. It would be useful to be able to detect vital signs, in particular heart rate, of subjects in a wide variety of settings beyond the clinical environment where the subject and environment may be less controlled. For example, being able to monitor a subject in a room, such as a secure room in a detention facility e.g. a prison or police cell, a room in a hospital or care home, or even room in the home, workplace or leisure facility such as a gym, but able to freely move within the room would be useful, but is much more difficult. In real life subjects mix periods of high activity and large movement with periods of relative immobility (seated or lying), will in general be clothed and have bedding to cover themselves. Thus, periods of inactivity while lying down, may coincide with the subject covering themselves partly or completely (known as "tenting") with bedding. Further, within rooms lighting conditions can vary with time, sometimes rapidly. Secure rooms are sometimes lit with visible artificial light and are sometimes completely dark with infrared being the only illumination available. Similar problems of movement and variable illumination occur also in fields such as fitness and health and well-being in the home or elsewhere. Existing systems do not provide vital signs monitoring or heart rate detection which can operate reliably in the face of these difficulties. Being able to detect the heart rate of a subject in these less controlled conditions would significantly improve the ability to monitor the well-being of such a subject and to comply with a duty of care requirement.

SUMMARY OF INVENTION

A first aspect of the invention provides a method of obtaining an estimate of a periodic vital sign of a subject from a video image sequence of the subject, comprising the steps of: detecting an image area with a strong intensity gradient in a frame of the video image sequence; defining a region of interest in the frame of the video sequence, the region of interest being defined not to include said image area; tracking the region of interest through other frames of the video image sequence; detecting intensity variations in said region of interest through the image sequence to form a time series signal and obtaining an estimate of said periodic vital sign from said time series signal.

The regions of interest defined to not extend over or include the areas of strong intensity gradients will correspond to visually flatter (i.e. more uniform intensity) regions of the image. This avoids the problem that movement of areas of higher image intensity variation can negatively affect the signal processing and create noise in the intensity variation signals which include the periodic signal of interest.

Preferably, the region of interest is defined as a square aligned with orthogonal axes of the frames of the video image sequence. Where the regions of interest are squares aligned with orthogonal axes of the frames of the image, it simplifies and speeds-up image processing, especially if image processing is performed on the integral image.

Preferably plural regions of interest are defined in each frame of the video image sequence.

The step of detecting an image area with a strong intensity gradient may comprise detecting an image area with an intensity gradient stronger than a predetermined threshold. The threshold may be based on the distribution of magnitudes of the intensity gradients in the image.

The step of tracking the region of interest through other frames of the video image sequence may comprise defining the position of the region of interest in other frames of the video image sequence by reference to detected image movement in the video image sequence. Such image movement in the video image sequence may be detected by measuring the optical flow in the video image sequence, e.g. by a dense optical flow algorithm, or by sparse optical flow, e.g. image feature tracking in the video image sequence, e.g. using a standard image feature tracking algorithm such as Lucas-Kanade.

The step of tracking the region of interest through other frames of the video image sequence may comprise detecting and tracking image feature points through the sequence; and the step of defining regions of interest may comprise defining regions of interest each of which is entirely within an area of the image between the feature points and which does not overlap the feature points.

By defining regions of interest which do not extend over or include the feature points, the regions of interest correspond to visually flatter (i.e. more uniform intensity) regions of the image. This avoids the problem that feature points— typically areas of higher image intensity variation—can negatively affect the signal processing and create noise in the intensity variation signals which include the periodic signal of interest. The feature points, on the other hand are useful for tracking through the image sequence and allowing the regions of interest that are defined with respect to them to be tracked through the sequence.

The method may further comprise the step of defining a grid of image areas whose vertices join the feature points and wherein each region of interest is defined to be entirely within a respective one of said image areas. The image areas may be polygons whose vertices are at the feature points.

The step of defining the grid of image areas may comprise defining the grid of image areas on one frame of the sequence and forming grids on the other frames of the sequence by joining the same feature points together. This produces consistent trackable regions of interest.

The grid may be triangular, each image area being a triangle, and this can be produced by a triangulation method such as Delaunay triangulation.

One way of forming the regions of interest is to define in-circles of said polygonal areas, these naturally avoiding the vertices themselves and thus avoiding the feature points. The regions of interest may be the in-circles or be based on them, e.g. be defined as squares co-centered on the in-circles.

In another embodiment plural regions of interest are drawn from a probability distribution made up of two components: one over region of interest size and one over region of interest location.

A second aspect of the invention provides a method of obtaining an estimate of a periodic vital sign of a subject from a video image sequence of the subject, comprising the steps of: defining a plurality of regions of interest in the frame of the video sequence, wherein plural regions of interest are defined by a probability distribution over region of interest size and a probability distribution over region of interest location in a frame of the video image sequence; tracking the regions of interest through other frames of the video image sequence; detecting intensity variations in said region of interest through the image sequence to form respective time series signals and obtaining an estimate of said periodic vital sign from said time series signals.

The location probability distribution may be defined in a process in which it is first initialized and then iteratively updated by reference to the quality of the time series signals obtained from nearby regions of interest.

Preferably the location probability distribution has a reduced probability density for image areas of higher intensity gradient and an increased probability density for image areas from which higher quality time series signals are obtained.

The method may further comprise the step of calculating a signal quality index representing the strength in said time series signals of said periodic vital sign and combining estimates from the regions of interest in dependence upon the signal quality index.

The method may further comprise the step of clustering said time series signals to form clusters of time series signals which have greater than a predetermined correlation and are obtained from regions of interest spaced by no more than a predetermined distance in the image, averaging the signals in each cluster, and obtaining the estimate of the periodic vital sign from the averaged signals.

The estimate of the periodic vital sign may be obtained by measuring the frequency, or the frequency of the strongest periodic component, of said time series signals or averaged signals.

The method may further comprise the step of applying principal component analysis to the time series signals or averaged time series signals, calculating a signal quality index of the principal components and obtaining the estimate by measuring the frequency, or the frequency of the strongest periodic component, of the principal component with the best signal quality index.

The intensity variations may include a periodic component corresponding to a photoplethysmogram signal, or may include a periodic movement signal.

The periodic vital sign may be the heart rate or breathing rate.

Another aspect of the invention provides apparatus for estimating a periodic vital sign of a subject comprising: a video camera for capturing a video image sequence of the subject; an image data processor for executing the method above; and a display for displaying the estimate of the periodic vital sign.

The invention also extends to a computer program comprising program code means for executing on a computer system the method above.

One embodiment of the invention provides a method and apparatus for estimating heart rate of a subject from a video image sequence of the subject. Regions of interest are generated by detecting and tracking feature points through the video image sequence, triangulating the feature points and generating square regions of interest corresponding to the in-circles of the triangles. The variation in intensity in each region of interest through the video sequence is taken as a time series signal, bandpass filtered in the physiologically expected range and the signals are clustered according to their similarity and spacing in the image. Signals in the same cluster are averaged together and for clusters with at least a preset number of signals, the frequency of the average signal is taken as indicating a heart rate. In an alternative embodiment, the intensity variations from the square regions of interest through the frame sequence are taken as time series signals and those signals which have a strong peak in the power spectrum are selected and subject to principal component analysis. The principal component with a highest signal quality is selected and its frequency is found and used to estimate the heart rate.

The invention will be further described by way of non-limitative example with reference to the accompanying drawings, in which:

FIG. 1 schematically illustrates a subject in a secure room and an apparatus in accordance with one embodiment of the invention;

FIG. 2 schematically illustrates example frames from a video image sequence and corresponding signals in FIG. 2B;

Figure 8:
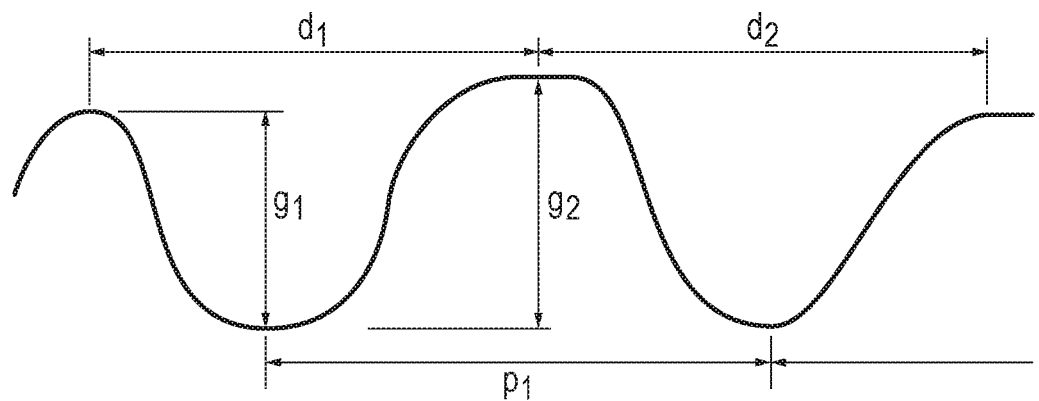
Figure 9:
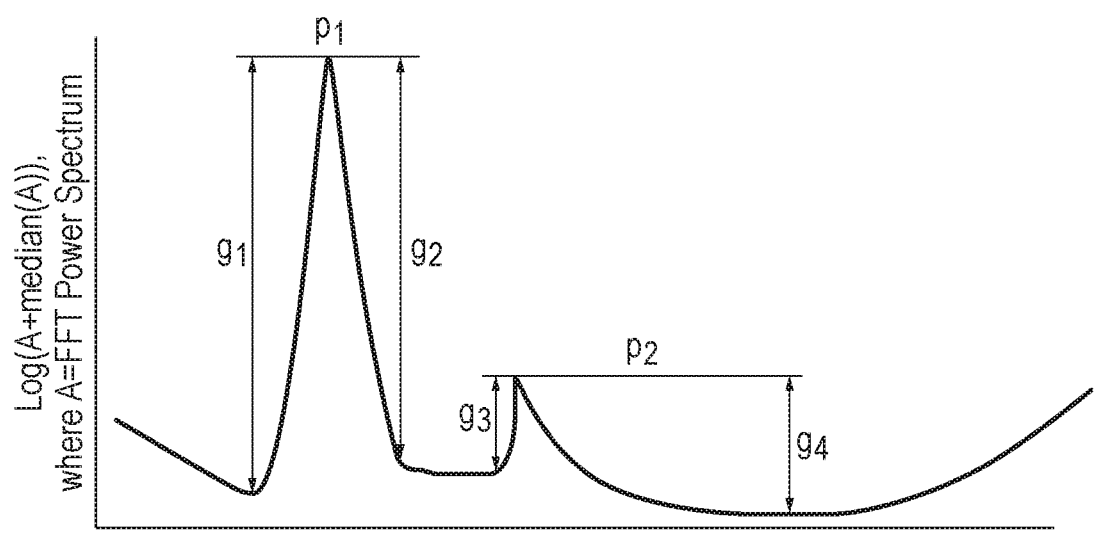
Figure 10:
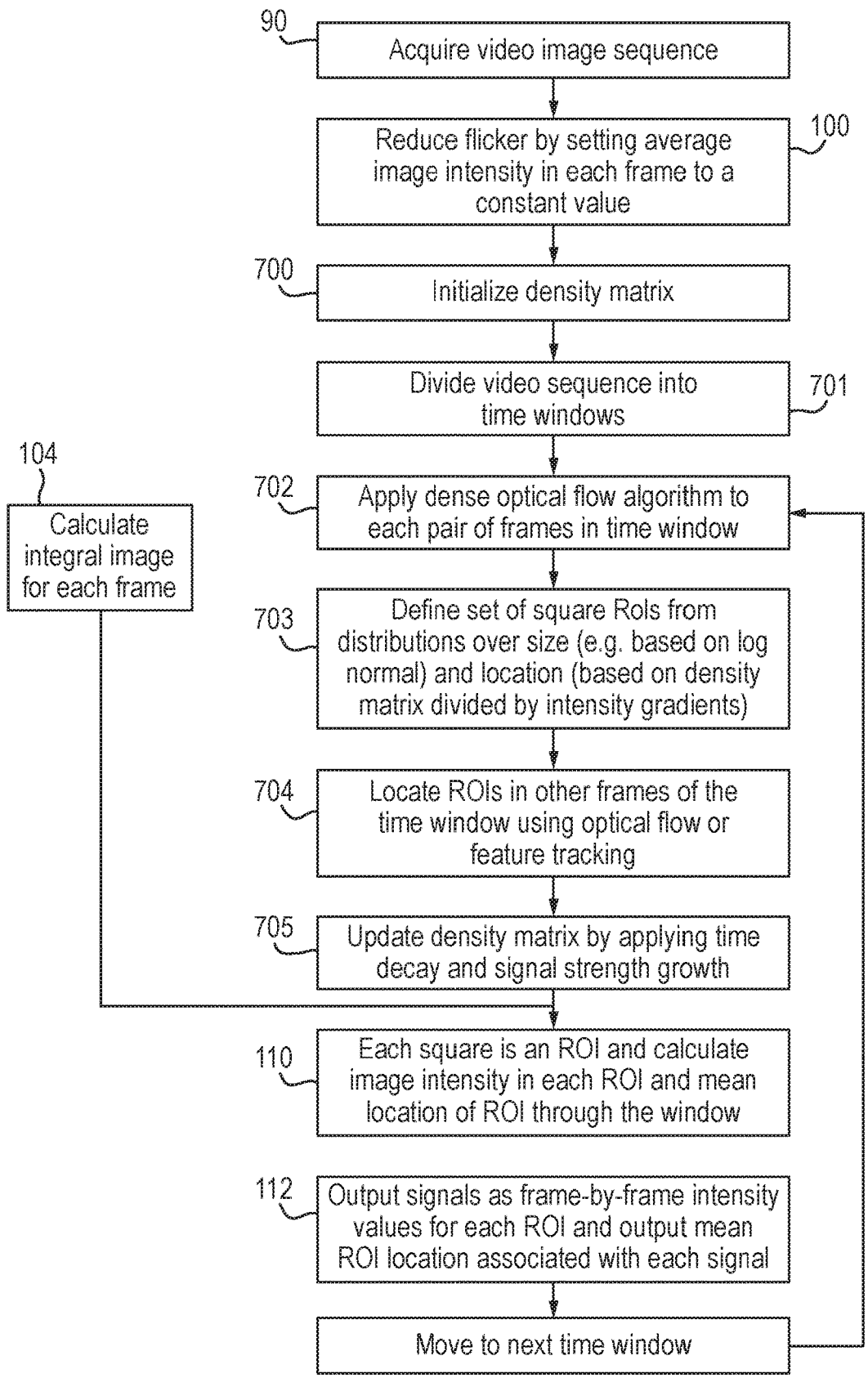
Figure 11:
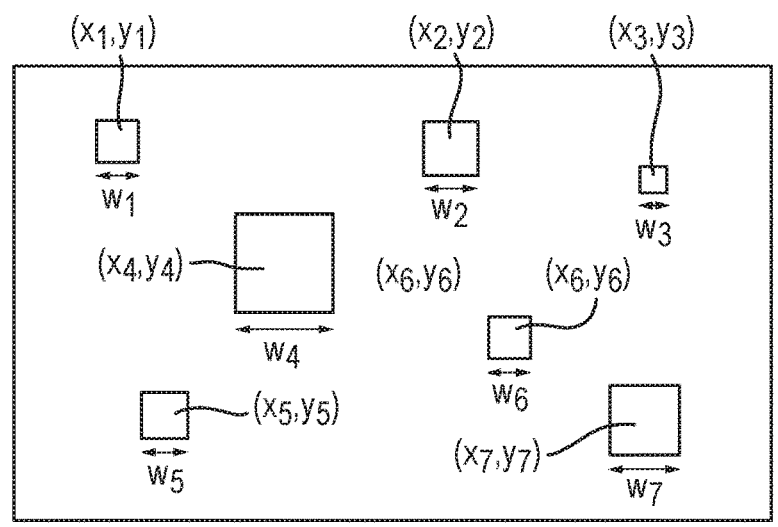
Figure 12:
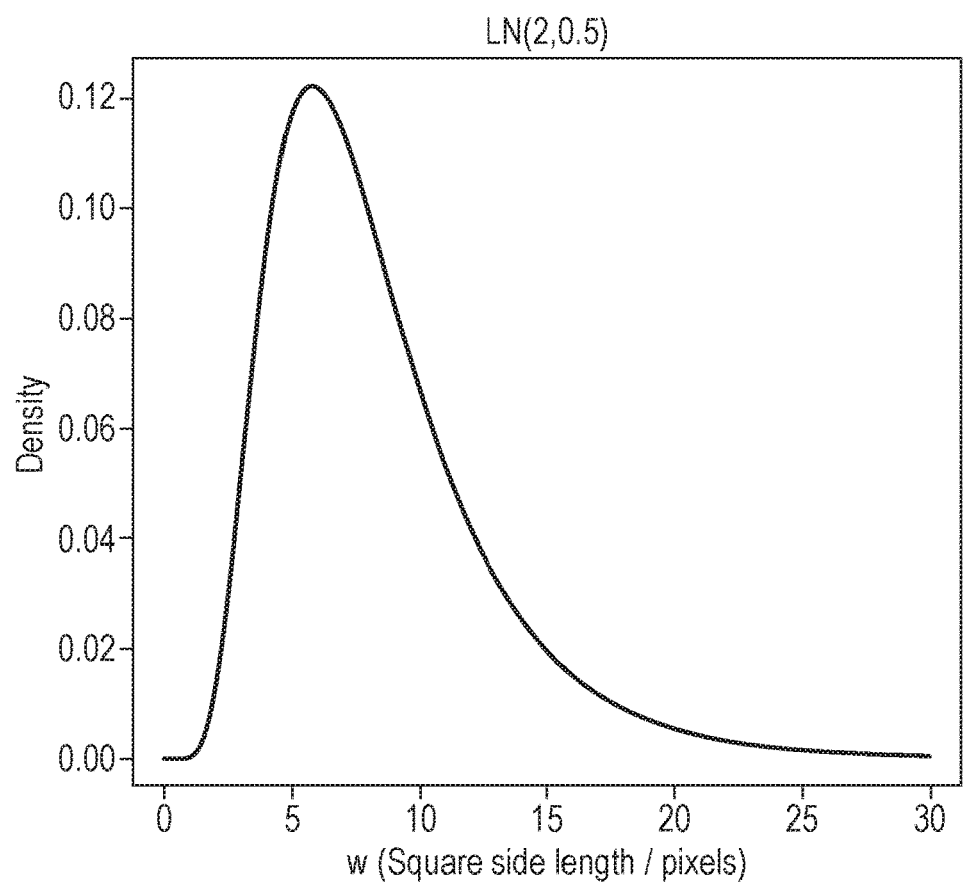

FIG. 8 schematically illustrates a signal and quantities used in calculating a signal quality index;

FIG. 9 schematically illustrates a power spectrum of a signal and quantities used in calculating a second signal quality index;

FIG. 10 is a flow diagram of signal processing in accordance with another embodiment of the invention;

FIG. 11 schematically shows a distribution of square regions of interest over an image frame;

FIG. 12 illustrates an example log normal distribution over width of region of interest.

Figure 1:
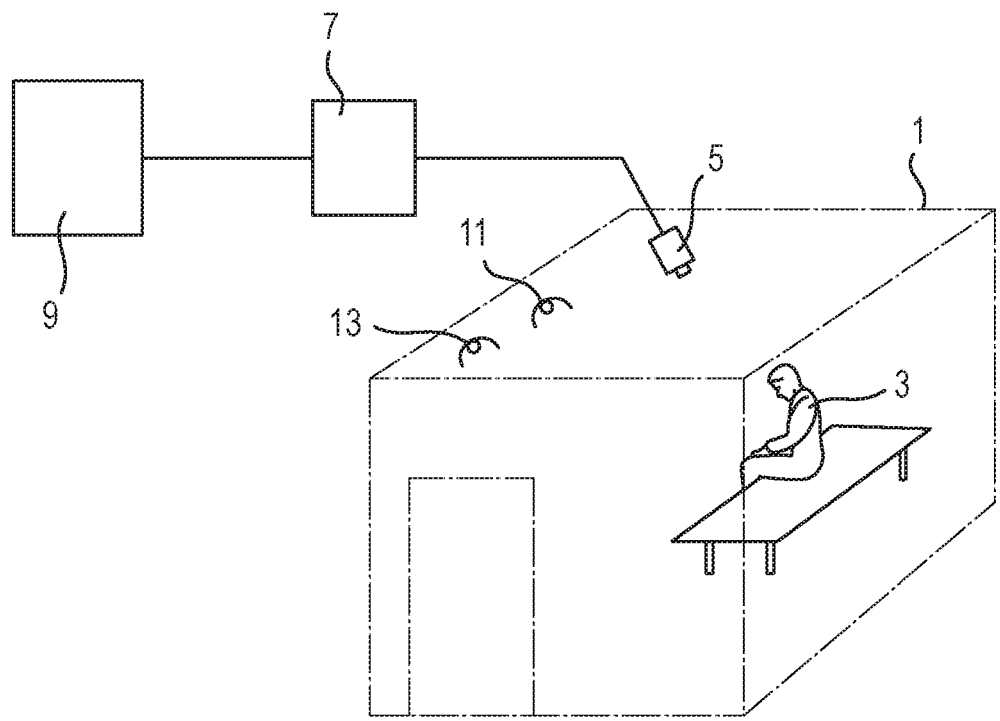

FIG. 1 schematically illustrates a secure room 1 occupied by a subject 3 who is monitored by a video camera 5 illuminated selectively by visible spectrum artificial lighting 11 or infrared lighting 13. The output from the video camera 5 is processed by a signal processor 7 and the results are displayed on a display 9. The results may be an estimate of the heart rate, or an indication that no heart rate can be detected, together with an indication of the length of time for which no heart rate has been detected.

The output from the video camera is a conventional digital video output consisting of a series of image frames, typically at twenty frames per second, with red, green and blue intensities across the image as an array of pixel values forming each frame. The red, green and blue sensors typically also provide a response in the infra-red (IR), allowing an IR signal to be obtained. Alternatively a monochrome digital video camera providing only one channel can be used—but such cameras also provide an IR signal. The video signal is analysed by a signal processor 7 which may be a programmed general purpose computer or a dedicated signal processing device and the display 9 can display the video image as well as other information, such as the estimated heart rate, or other vital signs obtained by analysis of the video image.

The processing of the video signals to obtain an estimate of the heart rate in accordance with one embodiment of the invention will now be described. This embodiment is based on detecting PPG signals in various regions of interest defined in the image frames. Thus the first aspect of this embodiment of the invention is the way in which the regions of interest in the video image are defined. Having defined regions of interest, the image intensities (e.g. average or sum) in the regions of interest through the frame sequence forming the video image then form time series signals which are analysed to detect a PPG signal.

Defining Regions of Interest (ROIs)

Figure 3:
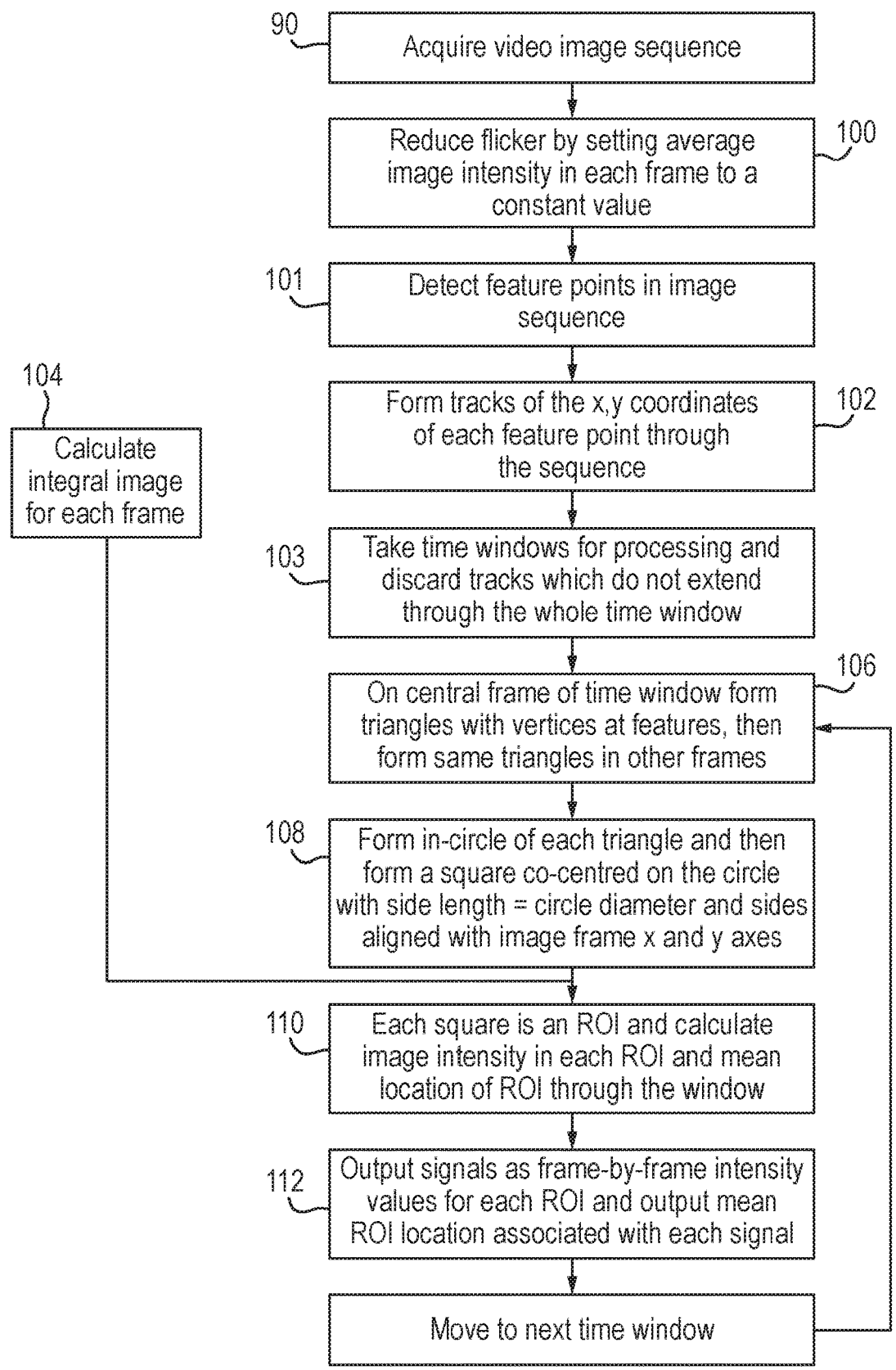
FIG. 3 is a flow diagram of signal processing in accordance with an embodiment of the invention.

FIG. 3 illustrates the signal processing for defining regions of interest in accordance with a first embodiment of the invention. Firstly, in step 100, the average frame intensity of each frame is set to a constant value to reduce image flicker, e.g. by multiplying each pixel value by the mean pixel value over the whole sequence and dividing by a constant to scale the values as desired (e.g. 0-255 for 8 bit values).

In step 101, feature points in the video sequence are detected. There are many ways of detecting feature points in a video sequence using off-the-shelf video processing algorithms based on sparse optical flow. For example, feature points consisting of recognisable geometrical shapes such as corner or edges can be detected based, for example, on the gradient of intensity variation in one or two dimensions, and any such conventional algorithm which identifies image feature points can be used in this invention. The feature points are tracked through the whole batch of video frames under consideration, e.g. by using a conventional tracking algorithm such as KLT tracking, to form "tracks" consisting of the x and y coordinates of each feature point in each image frame through the sequence. A measure of the strength of each feature point may also be calculated and stored associated with the feature points, for example corresponding to the strength of the image intensity gradient forming the feature.

In general feature detecting and tracking algorithms will generate many more candidate feature points than are required. Preferably in this embodiment the strongest feature point (as measured by gradient intensity) is used and then other feature points are taken in turn and either included or ignored based on their feature strength and spacing from already selected feature points, weighting them, e.g. proportionally, to their feature strength and their minimum distance in the sequence from already-selected feature points. This achieves a reasonably even distribution of feature points across the image. It is also preferable that the extent of movement of each feature through the image sequence under consideration is calculated (i.e. the variation in its x and y coordinates through the time window) and features for which the movement satisfies a predetermined definition of moderate, e.g. movement which is of the order of or greater than the typical movement found in a ballistocardiogram (BCG) and less than the gross level of movement which would preclude detection of a PPG signal, are preferred. This avoids selecting features which either do not move or which correspond to gross movement.

This process of detecting features and tracks through the time window and selecting them based on strength, movement and spacing continues until a desired number, for example several hundred, tracks have been selected.

In step 103 a time window (e.g. 6 seconds=60 frames at ten frames per second) is taken. Thus the next steps of the process are conducted on a time window of the video sequence, and then the process will be repeated for another time window shifted along by some time increment. The successive windows may overlap, for example if a six second window is stepped forwards by one second each time the overlap will be five seconds. An estimated heart rate is output (if detected) for each time window. Thus if the window is moved along by one second each time, a new heart rate estimate is, potentially, output every second.

A set of "persistent tracks" is defined as the set of all tracks that span all frames in the current window. In step 106, the central frame of the time window is taken and Delaunay triangulation is performed on the persistent tracks. Delaunay triangulation is a process which creates triangles favouring large internal angles. FIG. 2 illustrates schematically three successive frames at times n−1, n and n+1 with the central frame n having five feature points 20 connected to form triangles. As can be seen in FIG. 2, the position of the feature points varies from frame-to-frame. Having formed the triangles in the central frame of the sequence, the same triangles are formed in each other frame of the sequence (i.e. the same feature points are connected together) so that each triangle is defined throughout the whole six second time window by three KLT tracks specifying the positions of its vertices. In step 108, the in-circle 22 of each triangle is formed and then a square 24 concentric with the in-circle 22 is formed, aligned with the x and y axes of the image frame and with a side length equal to the diameter of the in-circle. Each of these squares 24 then constitutes a region of interest from which a signal will be obtained for further processing.

In a separate step 104, the integral image is calculated for each frame. As is well known in the art of image processing, in the integral image the value at any point (x, y) is the sum of all of the pixels above and to the left of (x, y), inclusive. The reason for using the integral images is that it simplifies and speeds up the image processing steps involving summing intensities and the steps in the method which involve such sums—e.g. step 110 are preferably conducted on the integral image, though they can be conducted on the original image frames with some loss of speed.

As illustrated in step 110 the intensity in each region of interest in each frame is calculated (the sum of all the pixel intensity values) and the intensity for each square region of interest (ROI) through the time window corresponds to a signal ($i_l$ to $i_m$) to be processed. In visible light, for a camera outputting three R, G, B colour channels, only the green channel is used. However if the room is illuminated by infra-red light, the mean of the three colour channels is used. The image intensity of each ROI through the frame sequence will typically vary as schematically illustrated in FIG. 2B. The mean location ($x_m$, $y_m$) of each square (for example the centre) is also calculated and associated with the corresponding signal $i_m$ over the time window. The intensity signals and associated locations are then output as time signals as illustrated in step 112.

Figure 7:
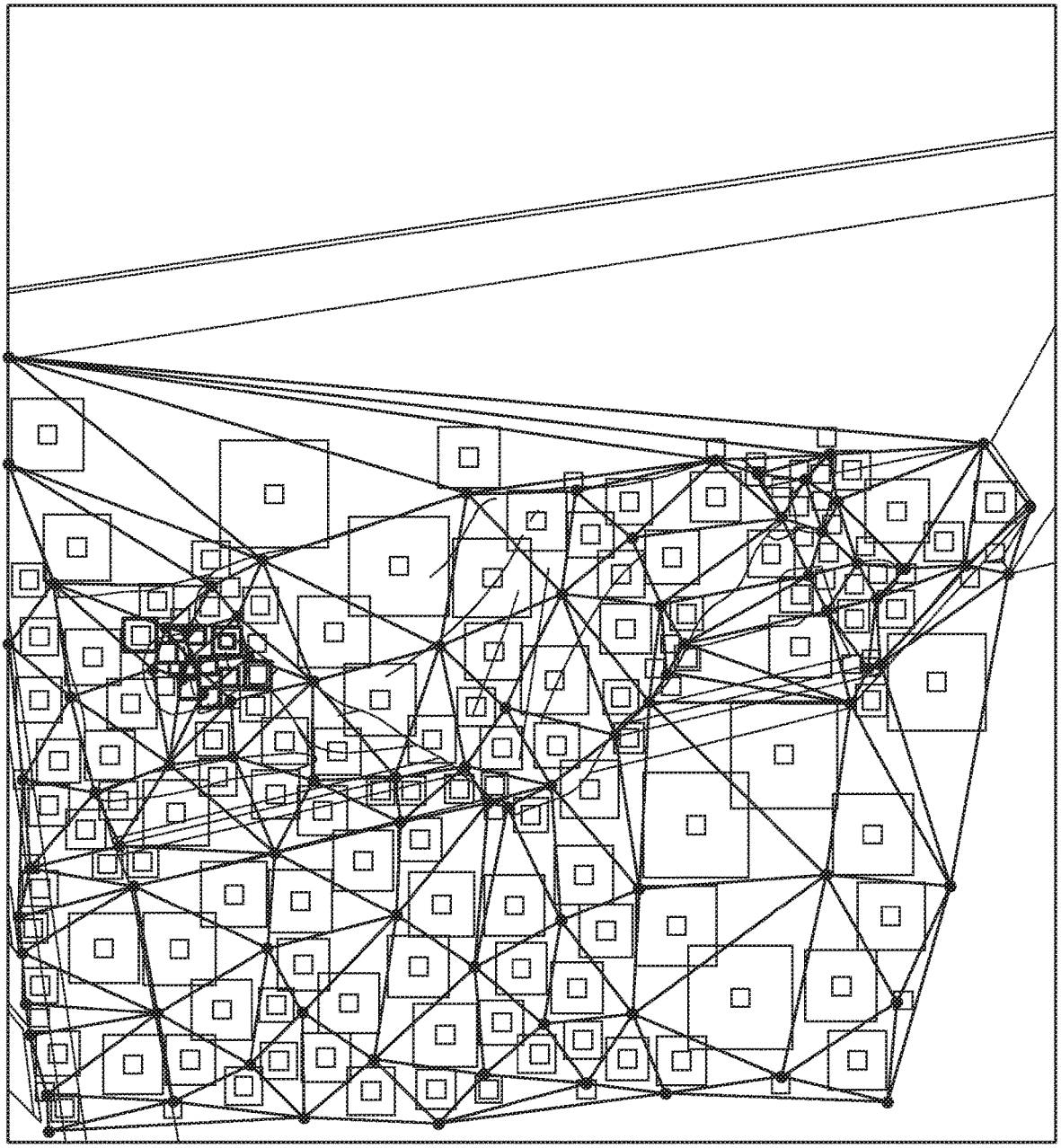
FIG. 7 is a frame of video data showing the results of signal processing in accordance with the method of FIG. 3.

FIG. 7 illustrates triangulation, and the corresponding squares on an actual video image frame.

The embodiment above is based on sparse optical flow. A second embodiment for defining ROIs will now be described based on using dense optical flow, this processing being illustrated in the flowchart of FIG. 10.

After the same initial steps 90 and 100 of acquiring a video image sequence and reducing flicker, in step 700 a density matrix is initialised, as a matrix of zeros of dimension equal to the video resolution. The density matrix will (after updating) quantify the amount of signal believed to have recently come from each image region (being a pixel and a small area around it) and it is used to influence the distribution of regions of interest used for each time window. It is only initialized at the start of the video sequence and is then used for all frames and time windows in that video sequence, being updated for each time window.

In this embodiment, for each time window (e.g. each set of 60 frames), the regions of interest are defined as image-axis-aligned squares of side length w and centred at position (x, y) in the image frame. A set number of regions of interest will be defined, typically from 100 to 500, e.g. 200. The regions of interest are defined by drawing their location and size randomly from probability distributions over (x, y) and w. FIG. 11 schematically shows a distribution of square regions of interest (seven for the sake of illustration) over an image frame centred at different positions ($x_1$, $y_1$) to ($x_7$, $y_7$) and with different sizes $w_1$ to $w_7$. The distribution of locations is a function of both the density matrix and image intensity gradients as explained below. The distribution of sizes (over w) is chosen to give a variety of different size squares appropriate to the video sequence to be processed (i.e. based on the scene and the set-up of the camera). For example, a log normal distribution may be used such as: LN(2, 0.5) as shown in FIG. 12. Such a distribution can be used an initial distribution which is then updated to shift towards values of w (side length) that provided better SQIs in previous windows. For example, suppose that during the previous window there were 200 squares with SQI values and w values ($s_1$,$w_1$), ($s_2$,$w_2$), ($s_{200}$,$w_{200}$). Then the new distribution over w could be set to LN(k, 0.5), where k=exp($\Sigma_i(w_i \log(s_i))$/200).

In step 701 the video sequence is divided into time windows as in the first embodiment, e.g. of 60 frames.

In step 702 a standard dense optical flow algorithm (such as Horn & Schunk or Farneback) is applied to each pair of consecutive video frames. For each pair of frames this generates a vector field corresponding to two matrices, each of dimension equal to the video resolution, representing the x and y movement associated with each location in the image, respectively.

In 703 the set of image axis-aligned square ROIs are defined as triples, (x,y,w) according to the distributions for location and size.

The distribution over locations is a function of both the density matrix and image intensity gradients as mentioned above. For the gradient contribution the absolute values of the intensity gradients are calculated in the central frame of the time window. These values are then smoothed spatially using a 2-D box filter to form a smoothed matrix of intensity values.

The distribution over (x,y) is then given by the density matrix divided by the smoothed matrix of intensity values (if all values in the density matrix are currently zero, e.g. as initialized, then a uniform distribution is used instead). The distribution thus favours image regions with a high density (density represents the quality of signals previously obtained from each image area) but with low image intensity gradients (i.e. favouring visually flatter image areas).

The (x,y) coordinates for the required number of square regions of interest are then randomly drawn from that distribution and they define the ROI locations in the final overlapping frame of the time window. The locations in other frames of the window are then obtained in step 704 by updating them by the frame-to-frame vector fields obtained in step 702.

In step 705 the density matrix is updated. First it undergoes a decay step in which each element in the density matrix is multiplied by some value, c, where 0<c<1 (larger values of c represent a less substantial decay. The value of c may be a constant. Alternatively c may depend on the extent of movement either globally (whole image) or locally (within the pixels near the element of the density matrix under consideration). Next the density matrix undergoes a growth step in which the elements of the density matrix near to signals with strong SQIs (see below) have their values increased. For each signal a Gaussian centred on the centre of the square to which that signal corresponds is added to the density matrix, with a weight that is proportional to the SQI corresponding to the signal and is on average about one tenth of the size of the density values.

Each of the squares is a region of interest and, as with the first embodiment, as illustrated in step 110 the intensity in each region of interest in each frame is calculated (the sum of all the pixel intensity values) and the intensity for each square region of interest through the time window corresponds to a signal ($i_l$ to $i_m$) to be processed. In visible light, for a camera outputting three R, G, B colour channels, only the green channel is used. However if the room is illuminated by infra-red light, the mean of the three colour channels is used. The image intensity of each ROI through the frame sequence will typically vary as schematically illustrated in FIG. 2B. The mean location ($x_m$, $y_m$) of each square (for example the centre) is associated with the corresponding signal $i_m$ over the time window. The intensity signals and associated locations are then output as time signals as illustrated in step 112.

In a variation of this embodiment, the array of square ROIs are generated (in one frame) according to the distributions over location and size as above, but then for the movement of the ROIs through the frames of the time window (i.e. their locations in other frames in the time window) feature tracking (e.g. KLT tracking) is used and the movement of the square ROIs is set to match the mean movement undergone by the three tracks that were closest to the given square during the central frame of the time window. The location distribution is updated for each time window in the same way as above using the density matrix which has a time decay and a signal strength growth, and the image gradients in the central frame of the time window.

Estimating Physiological Signals

The intensity signals output from step 112 of FIG. 3 or FIG. 10 will be further analysed to attempt to detect PPG, and in particular heart rate, signals. Two ways of achieving this will be described below.

Figure 4:
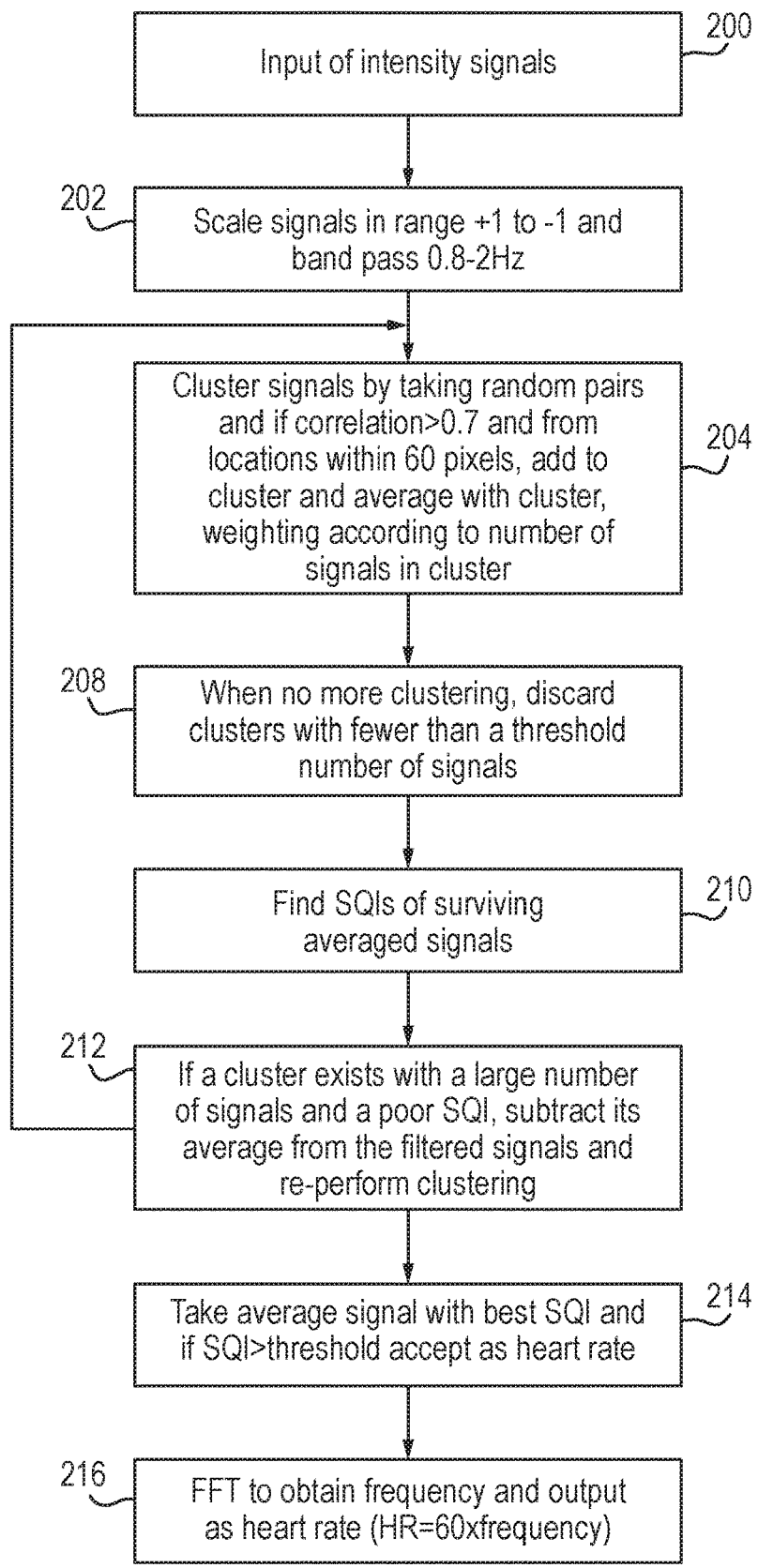
FIG. 4 is a flow diagram of signal processing in accordance with an embodiment of the invention.

In a first embodiment as illustrated in FIG. 4, the intensity signals such as those schematically illustrated in FIG. 2B are input in step 200 and the signals are scaled in the range of +1 to −1 and bandpass filtered in the expected physiological range for the heart rate of 0.8 to 2 Hz as illustrated in step 202. A standard bandpass filter such as a Butterworth filter may be used. The aim of steps 204 to 212 is then to combine together signals that are similar to form a smaller number of averaged signals. This is done by clustering, and in particular in step 204 a random pair of signals is selected and, if their Pearson correlation is greater than a threshold (for example 0.5) and if they are from locations within sixty pixels distance of each other in the image (Euclidean distance), the signals are averaged together and noted as being in the same cluster. The averaged signal then replaces the signals that formed it in the set of signals being considered for clustering.

The process of selecting random pairs of signals, or averaged signals, continues until no more combinations can be formed. It should be noted that as indicated in step 206, when already averaged signals are averaged together, they are weighted (e.g. in proportion) according to the number of original signals that formed them. In step 208, clusters with fewer than an empirically-set number, typically about ten, signals contributing are discarded and then in step 210 signal quality indices of the surviving average signals are calculated.

In this embodiment the signal quality index indicates how consistent the waveform is. For example such an SQI can be obtained by calculating the standard deviation of the peak-to-peak distance ($SD_{pp}$) the standard deviation of the trough-to-trough distance ($SD_{tt}$) and the standard deviation of the signal amplitude ($SD_{aa}$). A single signal quality index $SQ_1$ may be formed from these, e.g. as log $SD_{amplitude}$+max of (log $SD_{pp}$ or log $SD_{tt}$).

If a cluster exists which has a large number of signals in it, but a poor $SQI_1$, then in step 212 the averaged signal of that cluster is then subtracted from the original filtered signals output from step 202 and the clustering is re-performed. The subtraction is performed by linearly regressing each original signal against the average signal from the cluster, and each signal is replaced by its residuals from this regression, such that the correlation between the averaged signal and the result is zero. This step is effective to remove artifacts such as camera wobble or periodic lighting variations which affect the whole image.

In step 214, the averaged signal with the best $SQI_1$ is selected and, so as to remove spurious signals unlikely to relate to the cardiac cycle, accepted only if its $SQI_1$ is greater than a predetermined threshold. If accepted the signal and its frequency can be measured to output a heart rate estimate (heart rate in beats per minute=60×frequency in Hertz). As illustrated in step 216 one way of obtaining the frequency is to perform a Fast Fourier Transform and look for the highest peak in the power spectrum. Alternatively, the average peak-to-peak and trough-to-trough distances can be used, optionally discarding the first and last peaks and troughs in the time window.

If no cluster of signals survives the processing of FIG. 4, or if none of the surviving clusters provides an $SQI_1$ greater than the threshold, then no heart rate estimate will be made and instead an output indicating that no heart rate estimate is provided will be given. The processing then returns to step 200 for the next time window from the video image sequence (e.g. the next 9 second window moved along by an increment of 1 second).

Figure 5:
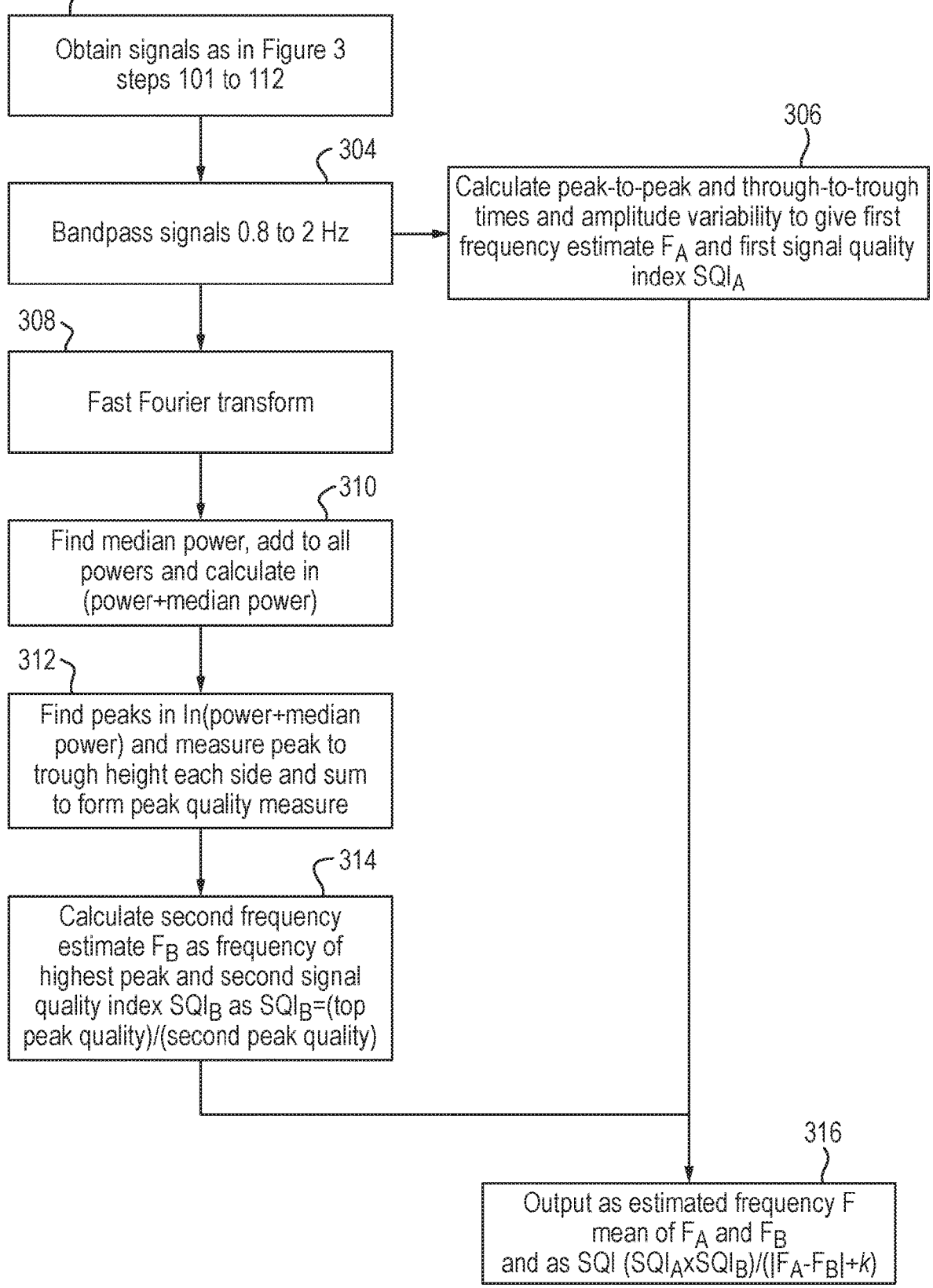
FIG. 5 is a flow diagram of signal processing in accordance with an embodiment of the invention.

FIG. 5 illustrates an alternative way of obtaining a heart rate estimate.

Then in step 302 intensity signals from each of the square regions of interest are obtained as shown in FIG. 3, and then in step 304 the signals are bandpass filtered in the passband corresponding to the expected physiological range of 0.8 to 2 Hz.

The process then calculates two different signal quality indexes for each of the signals. The first signal quality index $SQI_1$ is calculated in step 306 and is the same as the signal quality index calculated in step 210 of FIG. 4 and explained above. It is therefore based on the peak-to-peak and trough-to-trough and amplitude variability in the signal. A second signal quality index $SQI_2$ is obtained in step 308 to 314, this signal quality index relating to the strength of the main peak in the power spectrum of the signal. There are various ways of obtaining a measure of the strength of the highest peak in the power spectrum, but one way is as illustrated in steps 308 to 314. In step 308 the Fast Fourier Transforms of each of the signals is taken and in step 310, separately for each signal, the median power is calculated and added to the entire power spectrum. The natural log of the sum of the power and median power is calculated for each signal. FIG. 9 illustrates an exemplary plot for one signal. It is the peaks visible in this plot which will be analysed. In step 314, the peak to trough distance each side of the highest peak P1 are summed together ($g_1+g_2$) and the peak to trough distance either side of the second highest peak P2 are summed together ($g_3+g_4$), these sums forming peak quality measures. In step 314, the second signal quality index $SQI_2$ is calculated as the ratio of, or difference between, the peak quality measures of the highest and second highest peaks The power spectrum, as illustrated in FIG. 9, is also used to provide a measure of the dominant frequency in the signal, this being the frequency corresponding to the highest peak P1 in the plot.

Steps 308 to 314 therefore provide a second signal quality index $SQI_2$ and a second estimate of frequency. These can be combined with the first signal quality index $SQI_1$ and corresponding estimate of frequency obtained from the peak to peak, trough to trough and amplitude variability measures of step 306. As illustrated in step 316, the frequency of the signal is taken as a function of the two frequency estimates and the signal quality index of the signal, for example as:

$$SQI = \frac{SQI_2 \times SQI_1}{|F_1 - F_2| + k}$$

where k is a constant, which is high for a signal which has two good individual SQIs and for which the frequency estimates are close to each other. The constant k may be, for example, 5 for frequencies $F_1$, $F_2$ measured in beats per minute.

Figure 6:
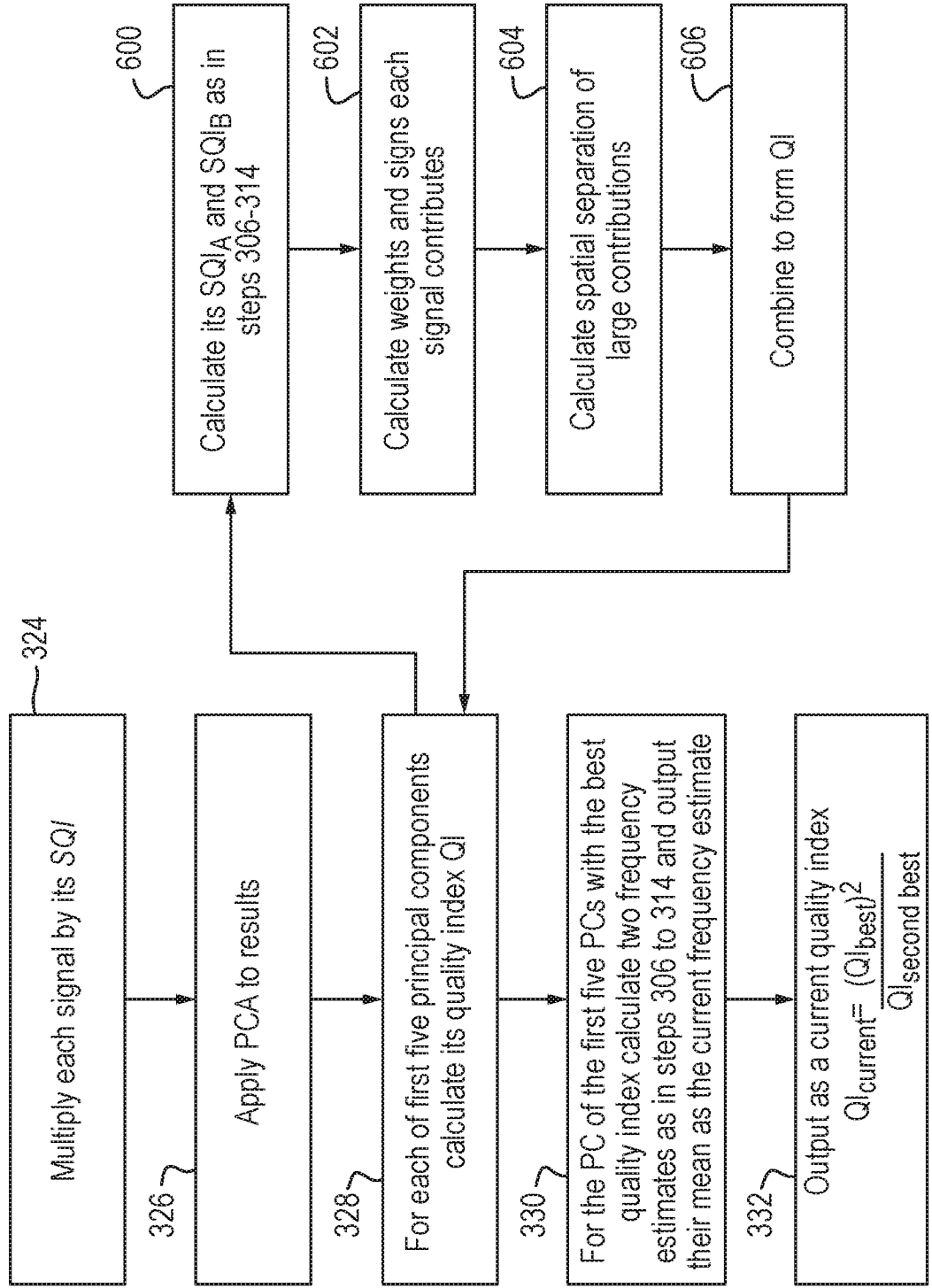
FIG. 6 is a flow diagram of signal processing in accordance with an embodiment of the invention.

Alternatively, as illustrated in FIG. 6, in step 324 each signal is multiplied by its signal quality index SQI, and then in step 326 principal component analysis is applied to the results. In step 328, for the first five principal components $PC_1$-$PC_5$, a new quality index QI is calculated based on a combination of: from step 600 the principal component's SQI, from step 602 the distribution of the principal component's weights; and, from step 604, 604 the distance between the ROI locations associated with the signals that contribute most towards the principal component.

The combination may be, for example, the sum A+B+C found by:

Let "A" be the SQI for the principal component.

Let "weights" be the vector of weights associated with the principal component.

Then let $B=1/(1-abs(sum(weights^3))/sum(abs(weights^3)))$, where abs(k) is the absolute value of k, for arbitrary k.

Let "C" be the mean Euclidean distance between the ROI locations associated with the four signals for with the greatest values of abs(weights).

In step 330 whichever of the first five principal components $PC_1$-$PC_5$ has the best quality index QI is selected and a frequency estimate and a quality estimate are output. The frequency estimate can be simply the highest peak in the power spectrum of the selected principal component, or can be obtained by measuring average peak-to-peak and trough-to-trough distances, or by taking the average of the two frequencies obtained from these methods and the principal component quality index can be obtained by taking the square of the principal component quality calculated in step 328 and dividing it by the principal component quality of the second best principal component.

The frequency estimate will be used to output a heart rate estimate (the heart rate in beats per minute equals 60 times the frequency in Hertz), and the quality index is output as a measure of the confidence of the measurement. The processing will then be repeated for the next time window.

The invention may be embodied in a signal processing method, or in a signal processing apparatus which may be constructed as dedicated hardware or by means of a programmed general purpose computer or programmable digital signal processor. The invention also extends to a computer program for executing the method.

The invention claimed is:

1. A method of obtaining an estimate of a periodic vital sign of a subject from a video image sequence of the subject, comprising the steps of:
    detecting an image area with a strong intensity gradient in a frame of the video image sequence;
    defining a plurality of regions of interest in the frame of the video image sequence, the regions of interest being defined not to include said image area;
    tracking the regions of interest through other frames of the video image sequence forming a time window consisting of a predetermined number of frames; and
    detecting intensity variations in said region of interest through the video image sequence to form respective time series signals and obtaining an estimate of said periodic vital sign from said time series signals,
    wherein
        the detecting of the image area with a strong intensity gradient and the tracking of the regions of interest through other frames of the video image sequence comprise detecting and tracking image feature points through the video image sequence and defining a set of persistent tracks as a set of all image feature point tracks that span all frames in the time window, and
        the defining of the plurality of regions of interest comprises defining regions of interest each of which is entirely within an area of an image between the tracked image feature points forming the persistent tracks and which does not overlap the tracked image feature points.

2. The method according to claim 1, wherein the regions of interest are defined as squares aligned with orthogonal axes of the frames of the video image sequence.

3. The method according to claim 1, wherein the step of detecting an image area with a strong intensity gradient comprises detecting an image area with an intensity gradients stronger than a predetermined threshold.

4. The method according to claim 1, wherein the step of tracking the regions of interest through other frames of the video image sequence comprises defining a position of the regions of interest in other frames of the video image sequence by reference to detected image movement in the video image sequence.

5. The method according to claim 4, wherein image movement in the video image sequence is detected by measuring optical flow in the video image sequence.

6. The method according to claim 1, further comprising the step of defining a grid of image areas whose sides join the image feature points and wherein each region of interest is defined to be entirely within a respective one of said image areas.

7. The method according to claim 6, wherein the image areas are polygons whose vertices are at the image feature points.

8. The method according to claim 6, wherein the step of defining the grid of image areas comprises defining the grid of image areas on one frame of the sequence and forming grids on the other frames of the video image sequence by joining same feature points together.

9. The method according to claim 6, wherein the grid is triangular, each polygonal image area being a triangle.

10. The method according to claim 6, wherein the regions of interest are defined by forming in-circles of said image areas.

11. The method according to claim 10, wherein the regions of interest are defined as squares co-centered on the in-circles.

12. The method according to claim 1, further comprising the step of calculating a signal quality index representing strength in said time series signals of said periodic vital sign and combining estimates from the regions of interest in dependence upon the signal quality index.

13. The method according to claim 1, further comprising the steps of:
    clustering said time series signals to form clusters of time series signals which have greater than a predetermined correlation and are obtained from regions of interest spaced by no more than a predetermined distance in the image;
    averaging the signals in each cluster; and
    obtaining the estimate of the periodic vital sign from the averaged signals.

14. The method according to claim 1, wherein the estimate of the periodic vital sign is obtained by measuring frequency, or frequency of a strongest periodic component, of said time series signals or averaged signals.

15. The method according to claim 1, further comprising the step of applying principal component analysis to the time series signals or averaged time series signals, calculating a signal quality index of principal components and obtaining the estimate by measuring frequency, or frequency of strongest periodic component, of one of the principal components with a best signal quality index.

16. The method according to claim 1, wherein the intensity variations include a periodic component corresponding to a photoplethysmogram signal.

17. The method according to claim 1, wherein the periodic vital sign is a heart rate or breathing rate.

18. An apparatus for estimating a periodic vital sign of a subject comprising:
a video camera for capturing a video image sequence of the subject;
an image data processor configured to
detect an image area with a strong intensity gradient in a frame of the video image sequence,
define a plurality of regions of interest in the frame of the video image sequence, the regions of interest being defined not to include said image area,
track the regions of interest through other frames of the video image sequence forming a time window consisting of a predetermined number of frames, and
detect intensity variations in said region of interest through the image sequence to form respective time series signals and obtain an estimate of said periodic vital sign from said time series signals,
wherein
the detecting of the an image area with a strong intensity gradient and the tracking of the regions of interest through other frames of the video image sequence comprise detecting and tracking image feature point tracks that span all frames in the time window, and
the defining of the plurality of regions of interest comprises defining regions of interest each of which is entirely within an area of an image between the tracked image feature points forming the persistent tracks and which does not overlap the tracked image feature points; and
a display for displaying the estimate of the periodic vital sign.

19. A computer program stored in a non-transitory computer readable medium in a computer system, a method comprising the steps of:
detecting an image area with a strong intensity gradient in a frame of a video image sequence;
defining a plurality of regions of interest in the frame of the video image sequence, the regions of interest being defined not to include said image area;
tracking the regions of interest through other frames of the video image sequence, forming a time window consisting of a predetermined number of frames; and
detecting intensity variations in said region of interest through the image sequence to form respective time series signals and obtaining an estimate of a periodic vital sign from said time series signals,
wherein
the detecting of the an image area with a strong intensity gradient and the tracking of the regions of interest through other frames of the video image sequence comprise detecting and tracking image feature points through the video image sequence and defining a set of persistent tracks as a set of all image feature point tracks that span all frames in the time window, and
the defining of the plurality of regions of interest comprises defining regions of interest each of which is entirely within an area of an image between the tracked image feature points forming the persistent tracks and which does not overlap the tracked image feature points.

* * * * *